United States Patent [19]

Pawelek et al.

[11] Patent Number: 5,225,435
[45] Date of Patent: Jul. 6, 1993

[54] SOLUBLE MELANIN

[75] Inventors: John M. Pawelek, Hamden, Conn.; Seth J. Orlow, Long Island City, N.Y.

[73] Assignee: Yale University, New Haven, Conn.

[21] Appl. No.: 674,489

[22] Filed: Mar. 25, 1991

Related U.S. Application Data

[63] Continuation-in-part of Ser. No. 603,111, Oct. 25, 1990, which is a continuation-in-part of Ser. No. 525,944, May 18, 1990.

[51] Int. Cl.$^5$ .......................................... A61K 31/405
[52] U.S. Cl. ........................................ 514/415; 424/59; 424/63
[58] Field of Search ...................... 424/59, 63; 514/415

[56] References Cited

U.S. PATENT DOCUMENTS 4,515,773  5/1985  Herlihy ............................... 514/785
4,968,497  11/1990  Wolfram et al. .................... 514/937

OTHER PUBLICATIONS

Korner & Pawelek, BA81(1): 5362 (1985).
Korner & Gettins, BA71(1): 3755 (1980).

Primary Examiner—Douglas W. Robinson
Assistant Examiner—Jean C. Witz
Attorney, Agent, or Firm—Sprung Horn Kramer & Woods

[57] ABSTRACT

A melanin that is soluble in an aqueous solution at a pH of at least 5 to 9 at a temperature of 0 to 100° C. The melanin is further characterized by being capable of being filtered through at least a 0.45 micron size filter. Still further, the melanin is characterized by having a molecular weight of greater than 10,000 kilodaltons. The melanin is useful for providing a naturally-appearing tan to mammalian skin and hair. Such melanin can be produced by combining dopachrome and 5,6-dihydroxyindole (or allowing dopachrome to spontaneously form 5,6-dihydroxyindole) and an appropriate enzyme or by combining 5,6-dihydroxyindole and 5,6-dihydroxyindole-2-carboxylic acid or by incubating 5,6-dihydroxyindole-2-carboxylic acid alone. The melanin is also useful for providing a sun-screen to mammalian skin and hair, to treat post-inflammatory hypo- and hyperpigmentation, to tint glass and plastic, to protect industrial materials against ultraviolet damage, and as a coloring agent in foodstuffs such as coffee, tea, soda, whiskey and liquors.

6 Claims, 6 Drawing Sheets

SOLUBLE MELANIN

CROSS-REFERENCE TO RELATED APPLICATIONS

This application is a continuation-in-part application of application Ser. No. 07/603,111, filed Oct. 25, 1990, now pending, which is a continuation-in-part application of application Ser. No. 07/525,944, filed May 18, 1990, now pending.

BACKGROUND OF THE INVENTION

1. Field of the Invention

The present invention concerns the synthesis of soluble forms of melanin and their composition, and methods of using such compositions to provide a naturally-appearing tan to mammalian skin and hair and to provide a sun-screen, to treat post-inflammatory hypo- and hyperpigmentation, to tint glass and plastic, and to protect industrial materials against ultraviolet damage.

2. Background Information

In biology, melanins are heteropolymers consisting of L-dopa and its enzymatic derivatives. They are ubiquitous in living organisms and are produced throughout the zoological and botanical phyla. In mammalian skin, melanins are produced through enzymatic processes in specialized cells known as "melanocytes". Melanins are the pigments of mammalian skin and hair.

Mammalian melanins are highly insoluble and can be dissolved (solubilized) only through non-physiological treatments such as boiling in strong alkali, or through the use of strong oxidants such as hydrogen peroxide. Tyrosinase, a key enzyme in the melanin biosynthetic pathway, can catalyze the formation of melanin in a test tube using L-tyrosine, L-dopa or 5′,6′-dihydroxyindole as substrates, however, the product is an insoluble precipitate as described above.

Ito, "Reexamination of the Structure of Eumelanin", *Biochimica et Biophysica Acta,* 883, 155–161, 1986, mentions natural melanin may be a polymer of 5,6-dihydroxyindole and 5,6-dihydroxyindole-2-carboxylic acid. Ito, however, does not teach or suggest combining these chemicals to form melanin.

Ito and Nicol, "Isolation of Oligimers of 5,6-Dihydroxyindole-2-carboxylic Acid from the Eye of the Catfish", *Biochemical Journal,* 143, 207–217, 1974, mention that oligimers of 5,6-dihydroxyindole-2-carboxylic acid exist in nature, for example in the tapetum lucidum of the sea catfish (Arius felis). Ito and Nicol, however do not teach or suggest that these structures could be used as a form of soluble melanin.

Palumbo, d'Ischia, Misuraca, and Prota, "Effect of metal ions on the rearrangement of dopachrome", *Biochimica et Biophysica Acta,* 925, 203–209, 1987, mention that the metal ions $Cu^{2+}$, $Ni^{2+}$, and $Co^{2+}$ are effective in inducing the non-decarboxylative rearrangement of dopachrome at physiological pH values, leading mainly to the formation of 15,6-dihydroxyindole-2-carboxylic acid. They suggest that when considered in the light of the known metal accumulation in pigmented tissues, their results provide a new entry into the regulatory mechanisms involved in the biosynthesis of melanin. Palumbo et al, however, do not teach or suggest that such metal ions could be used to affect the color or formation of soluble melanin. Likewise, Leonard, Townsend, and King, "Function of Dopachrome Oxidoreductase and Metal Ions in Dopachrome Conversion in the Eumelanin Pathway", *Biochemistry,* 27 6156–6159, 1988, present similar results to those of Palumbo et al regarding metal ions and the formation of 5,6-dihydroxyindole-2-carboxylic acid from dopachrome. Like Palumbo et al, Leonard et al also do not teach or suggest that such metal ions could be used to affect the color for formation of soluble melanin.

Many reports exist exploring the role of sulfhydryl compounds such as cysteine or glutathione in determining the red or yellow colors in melanin (see review by Pawelek and Korner, "The Biosynthesis of Mammalian Melanin", *American Scientist,* 70, 136–145, 1982). However these reports do not teach or suggest that said sulfhydryl compounds could be used to influence the colors of soluble melanins.

It would be of commercial value to have forms of melanin which are soluble at physiological pH and temperature. Such melanins could be applied evenly to mammalian skin and hair in appropriate vehicles without any of the caustic side-effects arising from the harsh reagents needed to solubilize precipitated melanins.

Such solubilized melanins could impart a naturally-appearing tan to mammalian skin and hair. Solubilized melanins would also be effective as sun-screens, since melanins are the chemicals in the skin which absorb ultraviolet radiation and thus provide protection from its harmful effects, such as premature skin aging and the occurrence of skin cancers.

Such solubilized melanins would be effective to treat post-inflammatory hypo and hyper-pigmentation due to eczema, acne, trauma, burns and psoriasis. Also, as a cover-up for vitiligo and other disorders of hypopigmentation, soluble melanins would be quite effective.

Since melanins absorb light throughout the ultraviolet and visible spectra, solubilized melanins would also be effective as glass or plastic tinting agents for eye glasses, contact lenses, car windows, house windows, office buildings, etc.

Likewise, by absorbing in the ultraviolet range, solubilized melanins would be effective agents to protect industrial materials against damage from ultraviolet radiation. By "industrial material" or "industrial product" is meant, for example, truck and car tires, paints, laminating materials, plastics, synthetic resins, and fabrics, particularly fabrics containing nylon, and like materials or products. It is well known that the rate of deterioration of paints, wood, plastics and rubber is dramatically increased by exposure to ultraviolet radiation.

SUMMARY OF THE INVENTION

It is the object of the present invention to provide solubilized forms of melanin at physiological pH and temperatures.

It is another object of the present invention to provide compositions and methods for applying such melanins to mammalian skin and hair to provide a naturally-appearing tan.

It is another object of the present invention to provide compositions and methods for applying such melanins to mammalian skin and hair to provide a sun-screen.

It is another object of the present invention to provide compositions and methods of applying such melanins to skin to treat hypo- or hyperpigmentation.

It is another object of the present invention to provide compositions and methods for applying such melanins to glass and plastic to provide tint.

It is another object of the present invention to provide compositions and methods for applying such melanins to industrial products to provide protection against ultraviolet radiation.

It is another object of the invention to provide coloring and/or flavoring agents based on soluble melanin for foodstuffs such as coffee, tea, soda, whiskey, liquor, and the like.

The above objects and other objects, aims, and advantages are satisfied by the present invention. The present invention relates to a melanin that is soluble in aqueous solution, e.g., water or an aqueous buffered solution, at a pH of at least 5 to 9, preferably 6.5 to 7.5, at a temperature of 0° to 100° C. The soluble melanin is further characterized by being capable of being filtered through at least a 0.45 micron size filter. The solubility of the melanin is in large part due to the abundance of carboxyl-groups.

The present invention also concerns a method of producing solubilized melanin comprising combining in a reaction mixture dopachrome and one or more enzymes derived from biological cells or tissues which have a pigmentary system. 5,6-dihydroxyindole may be added to the dopachrome and enzyme(s) or dopachrome may be allowed to spontaneously form 5,6-dihydroxyindole before adding the enzyme(s). Alternatively, the reaction mixture may comprise 5,6-dihydroxyindole-2-carboxylic acid alone or in a mixture with 5,6-hydroxyindole, in which case enzymes are not necessary and the reaction occurs in the presence of oxygen.

The color of the soluble melanin can be varied between black, brown, red and yellow by altering the contents of the reaction mixtures, for example by adding sulfhydryl containing compounds, or various metals such as, but not limited to, $Cu^{2+}$, $Ni^{2+}$, and $Co^{2+}$ or by altering the pH of the reaction mixtures.

The basis for the solubility of the melanin is in a large part due to the high degree of carboxyl groups present in the molecule, said carboxyl groups being incorporated as part of the 5,6-dihydroxyindole-2-carboxylic acid precursor. Compounds similar to 5,6-dihydroxyindole-2-carboxylic acid could substitute in providing said carboxyl groups and could therefore also act as precursors to soluble melanin.

The soluble melanin was synthesized non-enzymatically by mixing 5,6-dihydroxyindole (DHI) and 5,6-dihydroxyindole-2-carboxylic acid (DHICA). The closed diamonds represent a fresh, non-incubated mixture of DHI and DHICA where no soluble melanin was present. The open squares represent the same mixture incubated 18 hours at room temperature in the presence of oxygen during which time soluble melanin was synthesized.

The high absorbance peaking between 310-320 nm is characteristic of the presence of DHICA in the melanin. The broad absorbance over the range from 400-600 nm is due in the presence of visible color, characteristic of soluble melanin. Shown here are absorbance spectra in the "ultraviolet A" range and higher. Not shown are the strong absorbance spectra of the soluble melanin in the ultraviolet B and C ranges.

Figure 2:
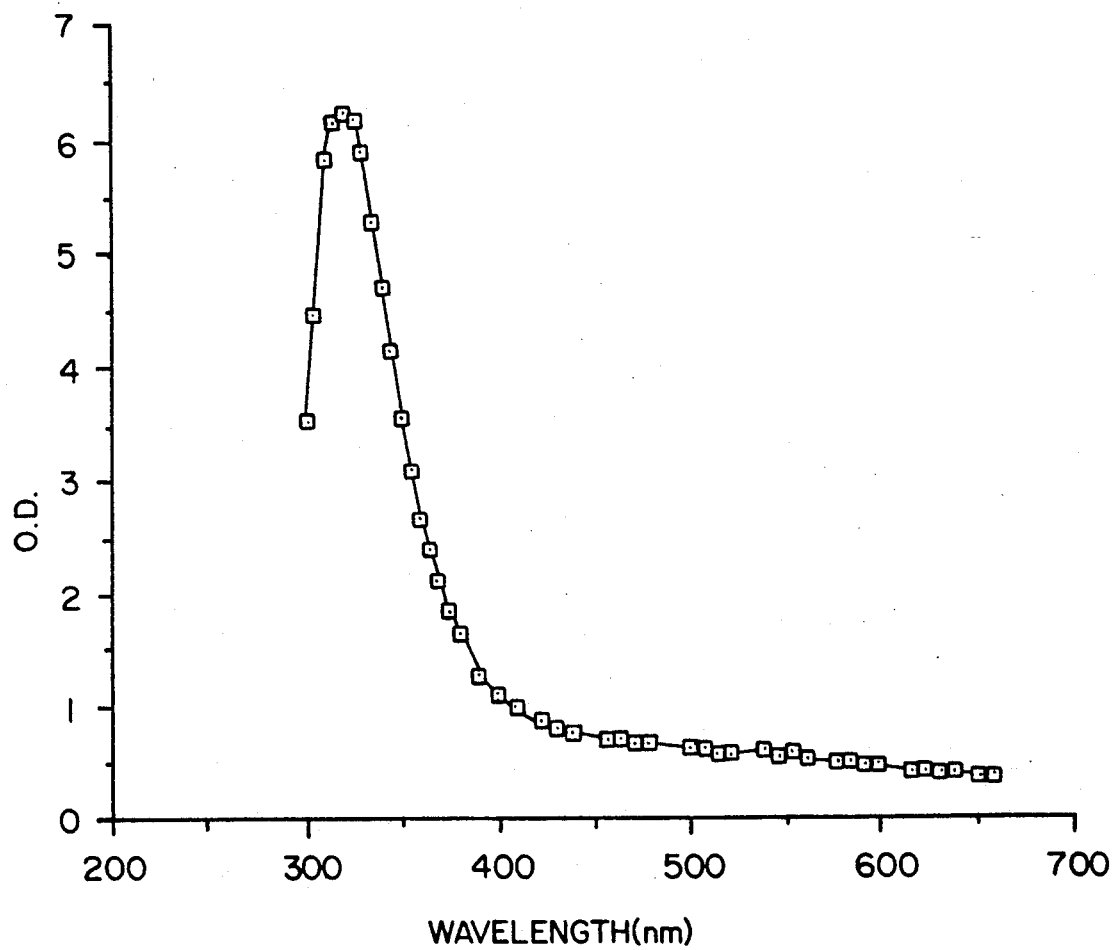
FIG. 2 depicts a graph showing the optical density (O.D.) of soluble melanin according to the invention at wavelengths greater than 300 nm.
Figure 3:
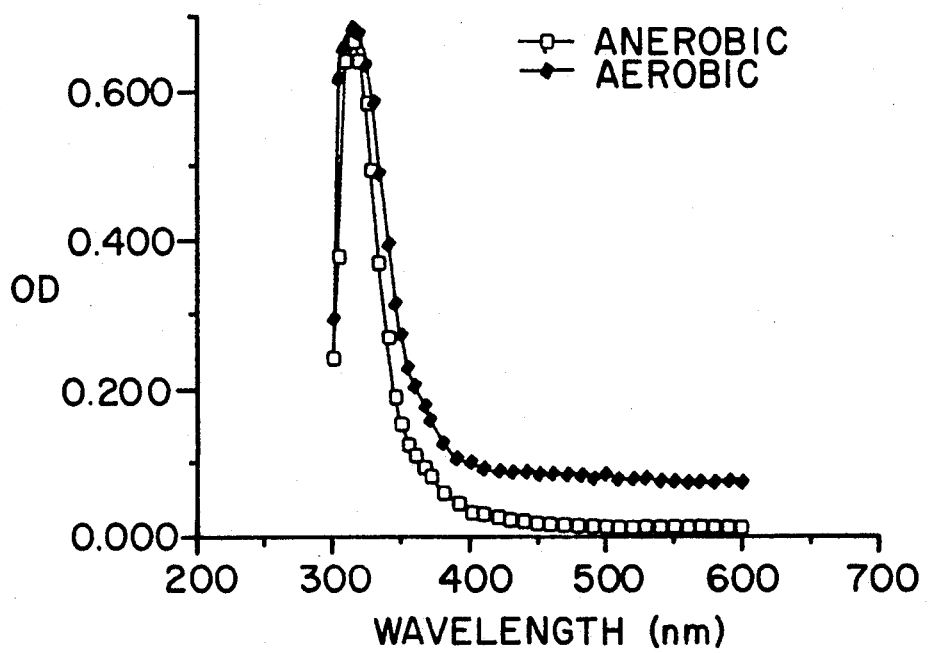

FIG. 3 depicts a graph showing the optical density (O.D.) of soluble melanin according to the invention at wavelengths greater than 300 nm. The soluble melanin was synthesized non-enzymatically as in FIG. 2 under either aerobic (closed diamonds) or anaerobic conditions (open square). It can be seen that oxygen increases the amount of absorbance in the 400–600nm range, i.e., the amount of visible color.

Figure 4:
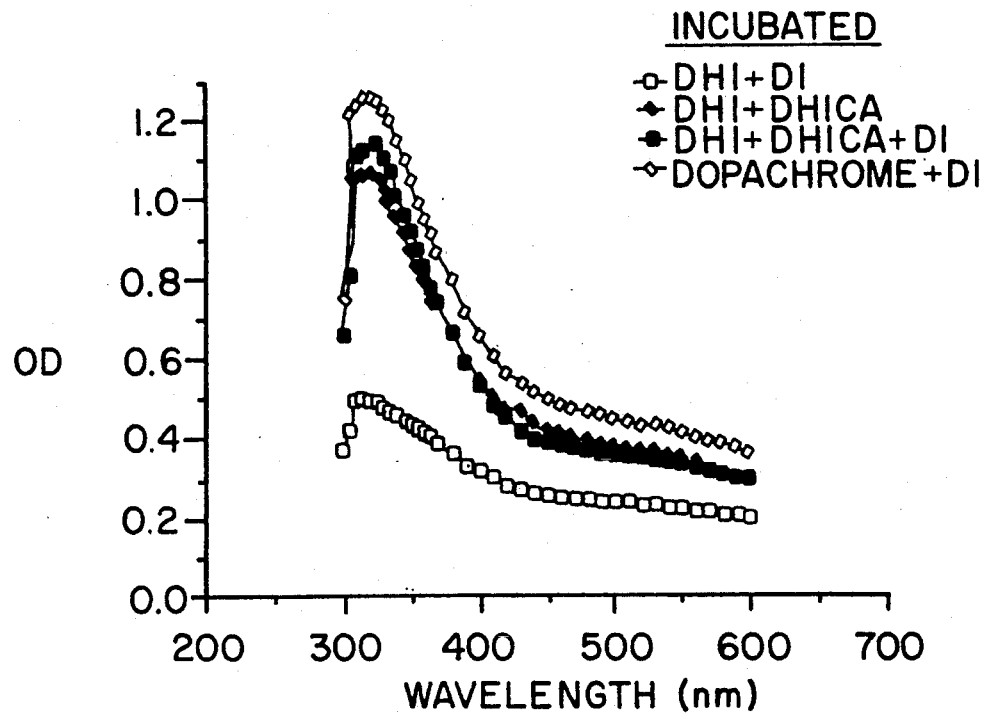

FIG. 4 depicts a graph showing the optical density (O.D.) of soluble melanin according to the invention at wavelengths greater than 300 nm. The melanin was synthesized either non-enzymatically by mixing DHI and DHICA (closed diamonds) as described in FIGS. 2 and 3; or enzymatically by mixing dopachrome isomerase enzyme complex (DI) with dopachrome and DHI (open diamonds), or by mixing DI with only DHI (open squares), or by mixing DI with DHI plus DHICA (closed squares). The results demonstrate that enzymatic and non-enzymatic methods for synthesizing soluble melanin yield comparable products. They also demonstrate the necessity of DHICA or a compound similar to DHICA in the reaction mixtures.

Figure 5:
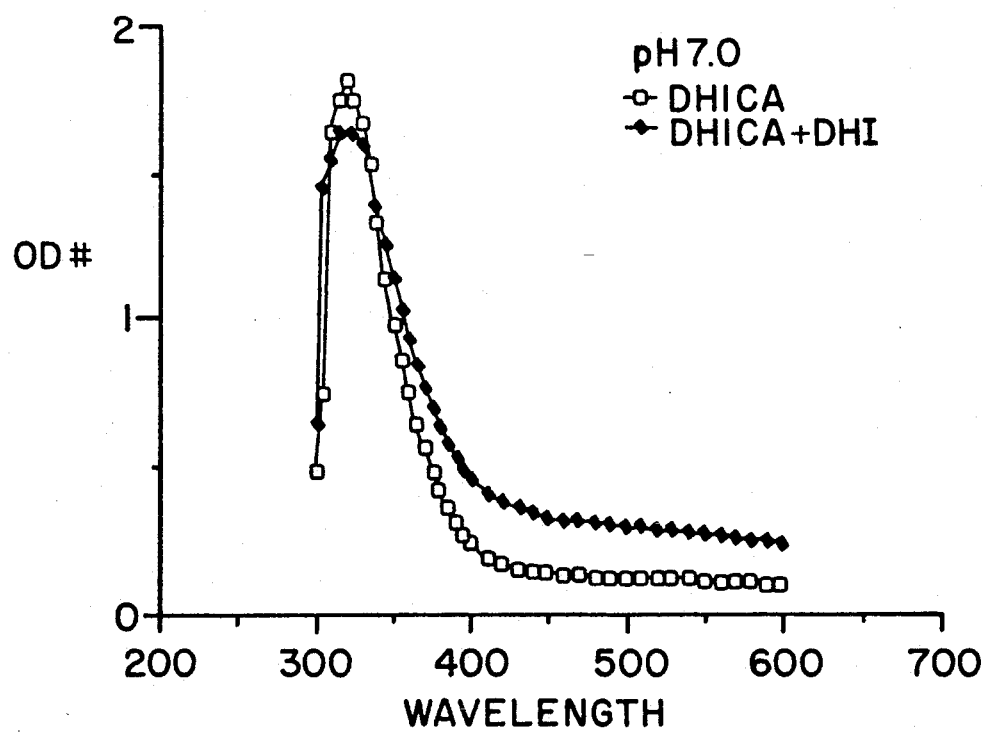

FIG. 5 depicts a graph showing the optical density of soluble melanin synthesized non-enzymatically at pH 7. The reaction mixtures were comprised of a mixture of DHICA and DHI (closed diamonds) or DHICA alone (open squares). The results demonstrate that at pH 7 more visible melanin (400–600 nm) is synthesized with a mixture of DHI and DHICA than with DHICA alone.

Figure 6:
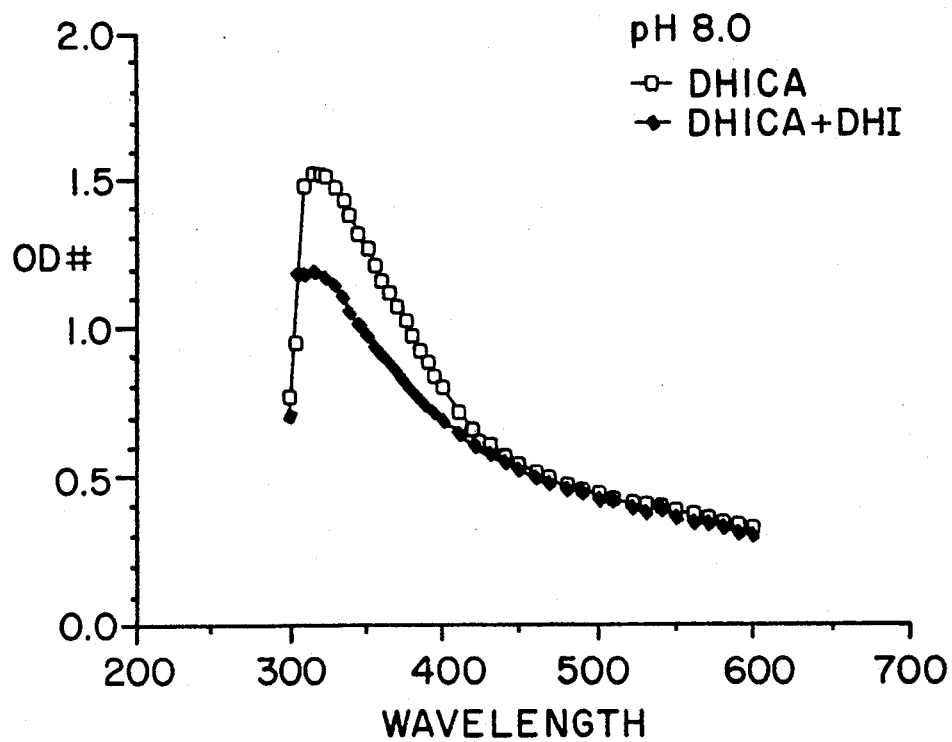

FIG. 6 depicts a graph showing the optical density of soluble melanin synthesized non-enzymatically at pH 8. The reaction mixtures are otherwise the same as those in FIG. 5. The results demonstrate that at pH 8, DHICA alone can serve as an efficient precursor to the formation of soluble melanin and in fact is somewhat superior to a mixture of DHICA and DHI.

Figure 7:
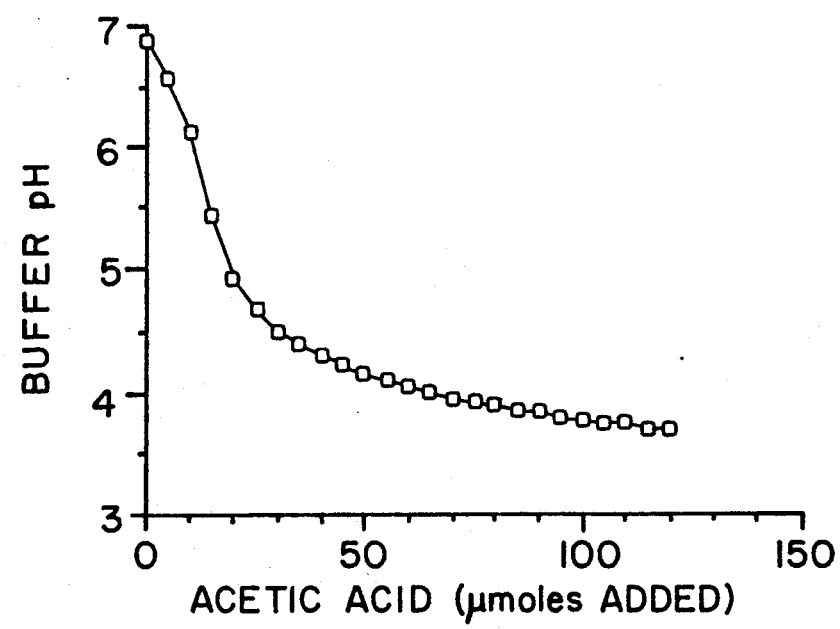

FIG. 7 depicts a graph showing a pH titration curve as increasing amounts of acetic acid are added to a solution of 2 mM soluble melanin.

Figure 8:
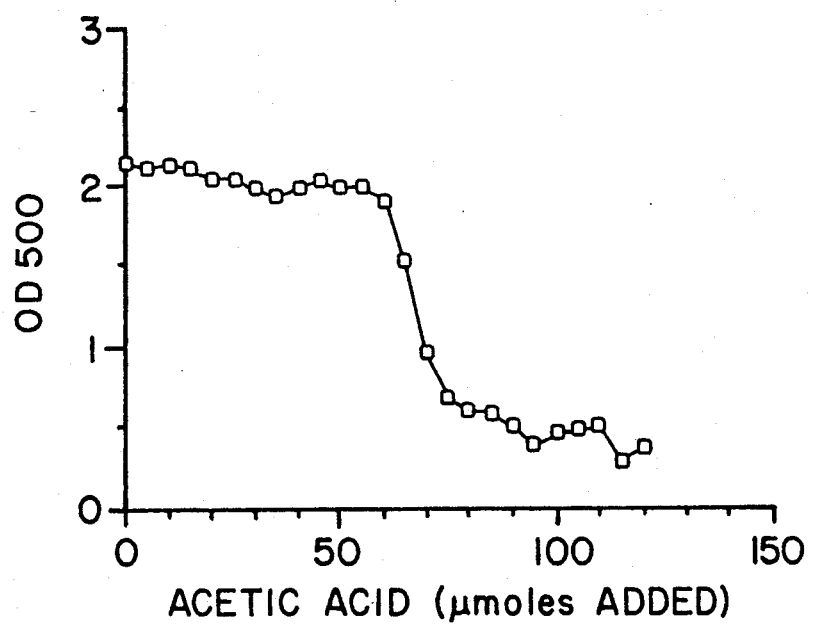

FIG. 8 depicts a graph showing the precipitation of soluble melanin during the pH titration shown in FIG. 7. For each point, acetic acid was added and the solution was allowed to sit at room temperature before being filtered through a 0.45 micron filter. The optical density of the filtrate was then determined at 500 nm. The soluble melanin begins to precipitate below pH4, i.e. as the pK of the carboxyl groups is reached. The results are consistent with the solubility of the melanin being determined by the number of non-protonated carboxyl groups present in the molecule.

DETAILED DESCRIPTION OF THE INVENTION

The soluble melanin of the invention remains in aqueous solution, at neutral pH (e.g., pH of 5 to 9, preferably 6.5 to 7.5), for long periods of time, e.g., indefinitely, at temperatures of 0° C. to 100° C., e.g., room temperature. The soluble melanin according to the invention is further characterized by remaining soluble upon freezing/thawing. The inventive soluble melanin is also characterized by being capable of being filtered through at least a 0.45 micron size filter. The soluble melanin according to the invention can be precipitated below pH4.

Following synthesis, the soluble melanin cannot be dialyzed through a semi-permeable membrane which allows the passage of molecules having less than a molecular weight of approximately 10,000. Therefore the soluble melanin according to the invention is of a molecular weight greater than 10,000, however, this is not an essential characteristic for its usefulness. The soluble melanin can be lyophilized to a dry powder form and then reconstituted to its soluble form with distilled water or suitable aqueous solvents, e.g., sodium phosphate 0.1 M or sodium chloride 0.1 M. It can also be reconstituted in organic solvents such as butanol or 2-butoxyethanol.

The soluble melanin according to the invention can be prepared non-enzymatically (synthetically) or enzymatically.

The enzymatic preparation according to the invention comprises combining in a reaction mixture a substrate, i.e., dopachrome, and one or more enzymes derived from biological cells or tissues which contain a pigmentary system and more particularly have the ability to produce melanin.

In the non-enzymatic preparation according to the invention, the reaction mixture comprises as a substrate 5,6-dihydroxyindole-2-carboxylic acid (DHICA) alone or a mixture of DHICA and 5,6-dihydroxyindole. Suitable analogs of DHICA, i.e. similar structures containing carboxyl groups, maybe substituted in the reaction. The enzymatic or nonenzymatic reaction mixtures may still further comprise as a substrate indole-5,6-quinone and/or melanochrome. Metal ions and sulfhydryl-containing compounds may be included.

The individual components of the substrate, be it one component, i.e., dopachrome, as in the enzymatic preparation, or more than one component as in the nonenzymatic preparation, preferably will be in an amount of 0.01 to 5.0 millimolar, but not necessarily limited to this concentration range. Stated otherwise, when more than one component is used, the components, i.e., a mixture of 5,6-dihydroxyindole and 5,6-dihydroxyindole-2-carboxylic acid, will preferably be in equal proportions or near to equal proportions.

The combining of substrate and enzymes or substrates in the reaction mixture is preferably conducted at a temperature of 15° C. to 37° C.

It is preferred in both the enzymatic and nonenzymatic preparation that oxygen, e.g., air or pure oxygen, be present. This is especially true for the nonenzymatic preparations.

Structural formulas and the relationship among some of the above described compounds are depicted as follows:

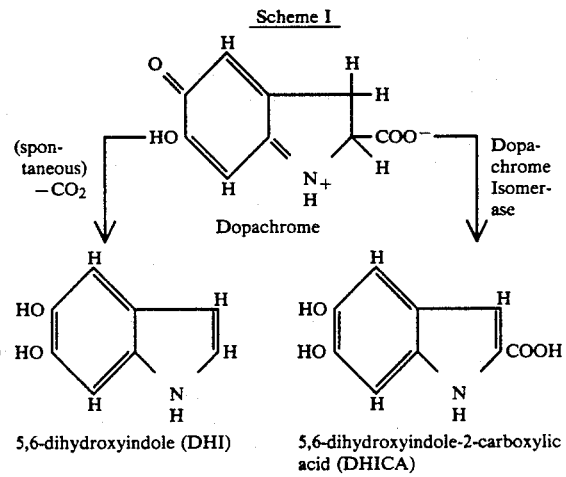

Scheme I

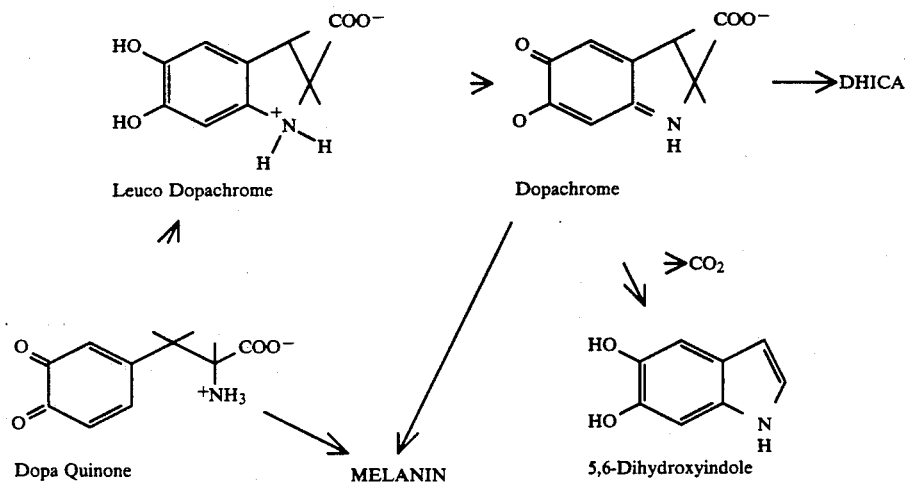

Scheme II

Scheme II

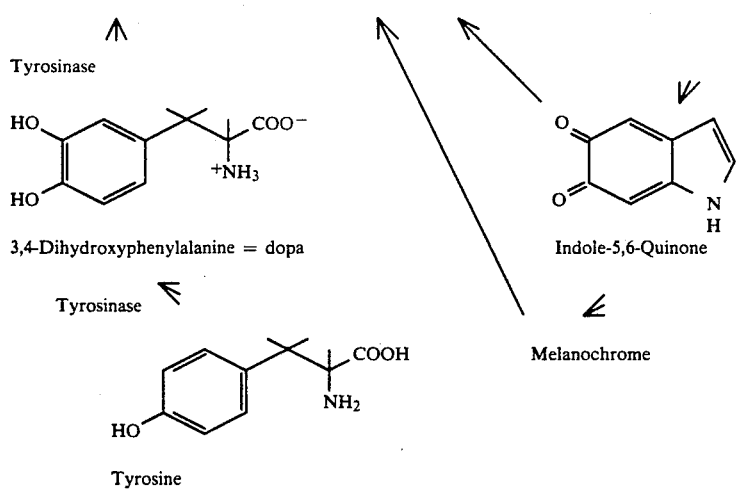

From the above it is seen that dopa quinone, leuco dopachrome, dopachrome, DHICA, 5,6-dihydroxyindole, indole-5,6-quinone, and melanochrome are all derivatives of dopa. Dopa itself is a derivative of tyrosine, so the above compounds are also derivatives of tyrosine (see Scheme II). Scheme I shows that dopachrome can give rise to 5,6-dihydroxyindole in a spontaneous non-enzymatic reaction, or it can give rise to DHICA in an enzymatically-catalyzed reaction. Copachrome can also give rise to DHICA in a metal-catalyzed reaction (not shown). The enzyme which catalyzes dopachrome to DHICA is named dopachrome isomerase and may indeed be the enzyme responsible for soluble melanin formation. The enzyme may also be a part of a complex comprising tyrosinase, dopachrome isomerase, glycoprotein 75, MSH receptor and other unknown proteins.

The above described enzymes are described in the following papers: tyrosinase: Ann Korner and John Pawelek, "Mammalian Tyrosinase Catalyzes Three Reactions in the Biosynthesis of Melanin", *Science*, 217:1163-1165, 1982; dopachrome isomerase: John Pawelek, "Dopachrome Conversion Factor Functions as an Isomerase", *Biochemical and Biophysical Research Communications*, 166:1328-1333, 1990; glycoprotein 75: Timothy M. Thomson, M. Jules Mattes, Linda Roux, Lloyd Old and Kenneth O. Lloyd, "Pigmentation-associated Glycoprotein of Human Melanomas and Melanocytes: Definition with a Mouse Monoclonal Antibody", *J. Invest. Derm.*, 85:169-174, 1985; MSH receptor: Seth J. Orlow, Sara Hotchkiss, and John M. Pawelek, "Internal Binding Sites for MSH: Analyses in Wild-Type and Variant Cloudman Melanoma Cells", *J. Cellular Physiology*, 142:129-136, 1990.

The enzyme may also include dopachrome isomerase and one or more of glycoprotein 75, MSH receptor and tyrosinase.

The enzyme may take the form of one or more individual enzymes or a complex of enzymes including tyrosinase, dopachrome isomerase, glycoprotein 75, MSH receptor and one or more additional enzymes which are distinct from the aforesaid four described enzymes, but which are capable of catalyzing the synthesis of soluble melanin.

The soluble melanin according to the present invention can be admixed with a physiologically acceptable carrier to form a composition, which has the uses previously noted.

Physiologically acceptable carriers useful in the practice of the invention are known in the art and non-limiting examples of such carriers include, for controlled release—microcapsules comprising carboxymethylene copolymers; for transdermal release—acrylamides; and for topical application—cosmetic bases.

In addition, if desired, the composition according to this embodiment comprises at least one additive selected from the group consisting of solvents, fragrances, sunscreening agents, preservatives and chelating agents.

Cosmetic bases useful in the practice of the invention are well known and include lotions, creams, ointments, lipstick, blush, cover-up, foundations and dusting powders. Examples thereof may be found in, e.g., U.S. Pat. Nos. 4,228,151; 4,282,206 and 2,949,403.

In the case that the inventive compositions are used as tinting agents for glass and plastic or as industrial product protecting agents, e.g. for protection against UV degradation, the inventive composition will be incorporated into the glass or plastic or industrial product. Simply by virtue of their soluble nature, the inventive compositions are easily incorporated in the glass or plastic or industrial product. For such uses the carriers, diluents, or the like, would not have to be physiologically acceptable. Other conventional agents for such uses could also be formulated therewith.

Solvents for use in accordance with the invention include, for example, ethanol, isopropyl alcohol, benzyl alcohol, oils, for example, ground nut oil, distilled and/or deionized water, physiological saline solution and the like. The specific solvent chosen will depend on the method of application.

It may also be desirable to add a preservative to the inventive compositions if they are to be used for topical applications. The preferred mode of administration of the inventive compositions is topical administration. Still further, the soluble melanin of the present invention may be combined with substances that stimulate the pigmentary system under conditions of low levels of UV light.

Preservatives are well known and may be exemplified by methylparaben, "DOWACIL 2000" and propylparaben.

If desired, in order to reduce the acidity or basicity of the inventive compositions, bases, acids or buffers may be added thereto in accordance with the knowledge of the art.

The concentration of soluble melanin in an aerosol, cream, lotion or other composition is preferably 0.01 mg/ml to 1.0 mg/ml, but not restricted to this concentration range.

Solutions have different colors depending on the concentration of "chromophore" dissolved in them. For example, a deep red solution will appear orange or pink when diluted with more solvent, but no additional chromophore. In the case of the soluble melanin, when it is dissolved at a fairly high concentration in water, e.g., 0.5 mg/ml, it appears brown-black in color. When more water is added so that the concentration of the soluble melanin is reduced to, e.g., 0.1 mg/ml, the solution appears golden in color. It is not believed that diluting the material changes any shift in the absorbance spectrum, rather it is believed to be a visual perception.

For the nonenzymatic preparation, the 5,6-dihydroxyindole-2-carboxylic acid and 5,6-dihydroxyindole may be maintained separately, for example, in microspheres, or in separate tubes or containers, until being mixed together on the skin of a mammal, e.g., human.

The soluble melanin can be made to adhere to the skin for several days and be resistant to water and soap simply by mixing the soluble melanin with any commercially available preparation of dihydroxyacetone, e.g., Lancome's Conque le du Sol oil ®. The DHA apparently acts as a cross-linking agent to covalently link the melanin with various factors, e.g., proteins, in the skin. It is likely that other cross-linking agents will achieve the same or better results.

The invention will now be described with reference to the following non-limiting examples.

EXAMPLE 1

Source of Enzymes

The enzyme preparation for the synthesis of soluble melanin can be obtained from any biological cells or tissues which have the ability to produce melanin, for example:

(1) extracts of vertebrate skins from horses, cattle, sheep, pigs, or any other such mammalian source; extracts of skins of fish, amphibian, reptiles, birds, or any other such vertebrate source;

(2) extracts of any botanical source which has the ability to produce melanin, such as mushrooms, potatoes, bananas, or any other such botanical source;

(3) extracts of invertebrate organisms such as worms, arthropods, or any such invertebrate source which has the ability to produce melanin;

(4) extracts of any single-cell organisms which have the ability to produce melanin, but which do not necessarily fall into a category of zoological or botanical, such as bacteria and protozoans;

(5) extracts of any organisms in which genes for enzymes producing soluble melanin have been genetically cloned; and (6) culture media of any organisms or cells which secrete enzymes for producing soluble melanin—such organisms or cells may or may not express cloned genes for the enzymes.

Furthermore, the source of biological material for the isolation of enzymes to produce soluble melanin does not necessarily have to be actively synthesizing melanin in vivo. A pigmentary system is defined as all or part of a group of enzymes which can recognize as their substrates precursors and/or intermediates in the melanin biosynthetic pathway. Some biological sources contain a pigmentary system, but do not synthesize melanin, however, extracts derived from them can produce soluble melanin. These biological systems, in their living state, are referred to as "amelanotic", or "non-pigmented". Many albino organisms fall into this category, i.e., they possess an incomplete or inhibited pigmentary system and do not make melanin in vivo, however, extracts from some albino organisms contain enzymes that can produce soluble melanin. Such organisms are also potential sources of enzymes for the production of soluble melanin.

EXAMPLE 2

Preparation of Enzymes

The enzymes for production of soluble melanin can be isolated from an extract of an appropriate biological source, or, from the culture media should the enzymes be secreted into the media by the source (see Example 1). Extracts are prepared by lysing the cells of the biological source through procedures such as homogenization (e.g., in a common kitchen "blender", in appropriate glass, metal, or plastic tissue homogenizers); such as freeze-thawing in a hypotonic solution such as water; or by any means which disrupt the cellular wall or plasma membrane of the biological source. In cases where the enzymes for producing melanin are themselves insoluble (e.g., in a particulate form within the cells), it may be necessary to lyse the cells in the presence of a non-ionic detergent such as "TRITON X-100", "CHAPS", or "TWEEN 80", or an organic solvent such as acetone or ethanol, or any other solvents which solubilize the enzymes, without destroying their ability to produce soluble melanin.

The following procedures may be useful, but are not mandatory for the preparation:

Extracts containing the enzymes in a soluble form can be clarified by filtration through such material as gauze or filter paper; or by centrifugation; or by "settling" through the use of natural gravitational force.

Extracts can be further clarified by mixing them with calcium phosphate (also known as "hydroxylapatite") which is itself insoluble, but which attaches to many molecular structures in cells, but does not attach to the enzymes for preparation of soluble melanin. The calcium phosphate and its attached molecules can be removed from the extract by filtration, centrifugation, or gravitational settling as described above. Although calcium phosphate is useful in this regard, the procedure is not restricted to the use of this agent only. Any insoluble compound which attaches to molecular structures other than the enzymes in question and does not destroy the activity of the enzymes can be employed.

Extracts can be further clarified by mixing them with an anion exchange agent such as diethylaminoethyl cellulose. At conditions around neutral pH (e.g., pH 6.5–7.5) and low buffer concentration (e.g., 5–10 millimolar sodium phosphate), the enzymes for production of soluble melanin will attach to such an anion exchange agent, while many other molecular structures will not. The enzymes in question can then be eluted from the anion exchange agent by increasing the salt concentration (e.g., by adding 0.4 molar sodium chloride, or by using a gradient of sodium chloride from 0 molar to 0.4 molar). Although diethylaminoethyl cellulose, sodium phosphate, and sodium chloride are useful in this regard, the procedure is not restricted to the use of these agents only. Any anion exchange resin, buffer, or salt which does not destroy the activity of the enzymes in question can be employed. The principle is the same.

Extracts can be further clarified by mixing them with an agent which attaches to glycoproteins, such as wheat germ lectin-sepharose. In mammalian cells, the enzymes in question are glycoproteins and therefore attach to such lectins, while many other molecular structures do not. The enzymes in question can then be eluted from the lectin by mixing with an appropriate sugar such a N-acetylglucoseamine, which causes a displacement of the enzymes from the lectin. Although wheat germ lectin-sepharose, and N-acetylglucoseamine are useful in this regard, the procedure is not restricted to the use of these agents only. Any appropriate lectin or sugar which does not destroy the activity of the enzymes in question can be employed. The principle is the same.

Extracts can be further clarified by applying them to columns containing molecular sieves such as Sephadex columns, or high pressure liquid chromatography columns containing molecular sieves. The enzymes in question can be eluted from such columns with non-destroying buffers according to their molecular weights and can be thereby separated from other molecular structures with differing molecular weights. Although Sephadex columns and various HPLC resins are useful molecular sieves, the procedure is not restricted to the use of these agents only. Any appropriate method for separation of molecules according to their molecular weights which does not destroy the activity of the enzymes in question can be employed. When each of the above procedures is carried out in the sequence listed, a preparation is obtained which contains the following: tyrosinase, dopachrome isomerase, a protein designated "glycoprotein 75" or "gp75", which exhibits catalase activity, and a protein designated "MSH receptor". That is, these four known proteins co-purify through the above procedures. Analyses by polyacrylamide gel electrophoresis indicate that there may be ten or more proteins in total. It is not presently known which protein or combination thereof catalyzes the synthesis of soluble melanin, although the synthesis can occur in the presence of phenylthiourea, a potent inhibitor of tyrosinase, suggesting that tyrosinase may not be necessary.

EXAMPLE 3

Enzymatic Synthesis of Soluble Melanin

Soluble melanin is prepared enzymatically by mixing the enzymes, isolated and purified as described above, with a solution containing dopachrome and 5,6-dihydroxyindole. The enzymes and the substrates are allowed to incubate in a non-destroying buffer (e.g., 0.1 molar sodium phosphate, pH 6.5-7.5) at ambient temperature or any suitable non-destroying temperature which allows for the reaction to occur (e.g., 15°-37° C.), until soluble melanin begin to appear (e.g., 3-6 hours). The reaction can be monitored visually or with the use of a spectrophotometer set in the visual spectrum (e.g., 400 millimicrons). When the reaction has reached completion, the salts from the buffer can be removed by dialysis and the soluble melanin can be stored at room temperature, frozen, or as a crystal or powder obtained through such procedures as natural evaporation or lyophilization. It is useful, but not mandatory, to enzymatically synthesize soluble melanin in the presence of a tyrosinase inhibitor such as phenylthiourea, because tyrosinase, which is occasionally present in the enzyme preparation, can cause the formation of insoluble melanin. Although phenylthiourea is a useful tyrosinase inhibitor because it does not inhibit or destroy the enzymes in question, the procedure is not restricted to phenylthiourea and any such tyrosinase inhibitor can be employed.

Soluble melanin prepared by the above procedure is golden-brown in color and absorbs widely throughout the ultraviolet and visible spectra (e.g., 220 to 700 millimicrons). The color can vary from brown-black in very concentrated solutions, to golden in more dilute solutions. The addition of sulfhydryl-containing compounds such as cysteine or glutathione can impart a reddish color to the soluble melanin.

Figure 1:
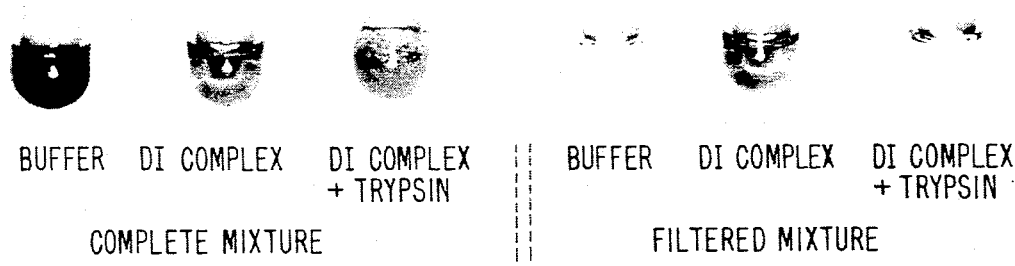
FIG. 1 depicts a photograph showing the enzymatic formation of soluble melanin according to the invention. Non-enzymatically formed soluble melanin is similar in composition to that seen in the tubes labelled "DI Complex".

FIG. 1 depicts the enzymatic formation of soluble melanin. The contents of the three tubes on the right were filtered through a 0.45 micron filter, otherwise they were identical in composition to the contents of the three tubes on the left. Considering the three tubes on the left:

1) The far left-hand tube contained a mixture of dopachrome, dopa and 5,6-dihydroxyindole. It also contained the buffer used to dissolve the enzymes (sodium phosphate 5 mM, pH 6.8, containing 20% glycerol vol/vol), but the enzymes themselves were not added.

2) The second tube from the left contained the same mixture as in the left-hand tube, but in addition it contained the enzymes dissolved in their buffer. The enzymes are referred to as "DI Complex".

3) The third tube from the left was identical to the middle tube, but also contained trypsin, a potent proteolytic enzyme, at a concentration of 0.5 mg/ml.

The three tubes on the left were incubated at room temperature for 6 hours before half their contents were removed and filtered as described above into the three right-hand tubes.

It can be seen that with buffer only, all the black melanin which formed was trapped on the filter, i.e., insoluble. When the DI Complex was added, the golden-brown melanin was completely filterable, i.e., soluble. When trypsin was present, no soluble melanin was formed, indicating that the soluble melanin production was catalyzed by a protein (enzyme). Melanin prepared non-enzymatically are similar in appearance to those seen in the tubes labelled "DI Complex".

The soluble melanin provided in Example 3 have the following characteristics:

(1) are greater than molecular weight 10,000,
(2) are stable to boiling,
(3) are stable to freezing,
(4) can be filtered through a filter at least as small as 0.45 microns,
(5) are soluble in water at a pH range of at least 6.5 to 7.5 at temperatures from 0° to 100° C.,
(6) can be precipitated below pH 4,
(7) can be lyophilized to a crystal/powder form which can be redissolved in water,
(8) vary from brown-black to golden in color depending on concentration,
(9) absorb throughout the ultraviolet and visible spectra and
(10) can be prepared in red and yellow forms with the addition of sulfhydryl-containing compounds and various metal ions.

EXAMPLE 4

Non-Enzymatic Synthesis of Soluble Melanin

Soluble melanin can be prepared in a nonenzymatic reaction by mixing 5,6-dihydroxyindole-2-carboxylic acid (DHICA) and 5,6-hydroxyindole (DHI) in the presence of oxygen in a non-destroying buffer (e.g., 0.1 molar sodium phosphate, pH 6.5 to 7.5) or by incubating DHICA alone at ambient temperature of any suitable non-destroying temperature which allows the reaction to occur (e.g., 15 to 37° C.), until soluble melanin begins to appear (e.g., 3 to 6 hours). The soluble melanin thus formed is indistinguishable from that which is formed enzymatically as described in Example 3.

The difference between enzymatic and non-enzymatic synthesis of soluble melanin is that in the enzymatic synthesis, 5,6-dihydroxyindole-2-carboxyl acid is produced from dopachrome by the enzyme dopachrome isomerase, and 5,6-dihydroxyindole is produced spontaneously from dopachrome, while in the non-enzymatic synthesis, 5,6-dihydroxyindole-2-carboxylic acid (DHICA) and 5,6-dihydroxyindole are mixed directly to form soluble melanin or DHICA is incubated alone. In both the enzymatic and non-enzymatic procedures, the reaction is greatly enhanced by the presence of oxygen.

However, once DHICA dissolves, it begins to spontaneously convert to soluble melanin. If it is to be used on the skin, then it should be in an oxygen-free vehicle. Accordingly, when not in use, store DHICA in a freezer, weighing out small amounts at time of use. DHICA is much more stable at pH 6 than pH 8.

EXAMPLE 5

Spectrophotometric Quantitation of Soluble Melanin

Melanin was synthesized using a mixture of L-dopa, dopachrome, dihydroxyindole, and dihydroxyindole-2-carboxylic acid at concentrations of approximately 0.4 mg/ml dissolved in sodium phosphate, 0.1 M, pH 6.8. The "DI Complex" enzymes purified approximately 2,000 fold from 0.5 grams mouse melanoma tissue (see Example 3) were dissolved in buffer (sodium phosphate, 5 mM, pH 6.8) and incubated in a 4 ml reaction mix with the above substrates at room temperature for 5 hours. The control reaction had buffer only, with no enzymes added. In both reactions, melanin formation occurred, but when the enzymes were present, the melanin could be filtered through a 0.45 micron filter, whereas in the presence of buffer only, the melanin was insoluble and could not be filtered. Solutions were diluted 50 fold before measuring the optical density. A photographic representation of this experiment is seen in FIG. 1.

FIGS. 2 to 4 show the optical spectrum of soluble melanin according to the present invention. In FIGS. 2 to 4, the melanin exhibited a peak optical density (O.D.) at a wavelength of 310-320 nm. The spectra and O.D. were the same after the melanin had incubated under sterile conditions for 2 months at room temperature (20° C.), and whether or not the melanin was dialyzed or filtered through a 0.45 micron filter.

Note in FIG. 4 that relatively little soluble melanin is made when DHI plus DI are mixed together in the absence of any other added substrates. Note also, when DHI plus DHICA are mixed together they make as much soluble melanin as when they are mixed additionally with DI, i.e., DI is not necessary in this case. Finally, note that a mixture of dopachrome and DHI in the absence of DI results in an insoluble precipitate (not shown here), but in the presence of DI results in the synthesis of soluble melanin. This is because DI converts dopachrome to DHICA which then in turn combines with DHI in the presence of oxygen to form soluble melanin. In the absence of DI, dopachrome spontaneously converts to DHI and a precipitate (insoluble melanin) forms (see Scheme I hereinabove).

TABLE I

| Spectrophotometric Quantitation of Soluble Melanin | | |
|---|---|---|
| | Optical Density at Wavelength 320 nm | |
| Synthetic Route | Before Filtration | After Filtration |
| Buffer only (no enzymes added) | 1.22 | .024 |
| Enzymes added | 0.982 | 0.966 |

EXAMPLE 6

Transdermal Release Composition

An admixture is prepared comprising the following

| | Parts by weight |
|---|---|
| Acrylamide copolymer (e.g., "polytrap FLME 203") | 20 |
| soluble melanin, as prepared according to Examples 3 or 4 | 5 |
| Alcohol | 74.9 |
| and a fragrance | 0.1 |

The above mixture is applied to the skin, once a day, preferably in the morning, for two to four weeks.

EXAMPLE 7

Tanning Oil

An admixture is prepared by adding in the order indicated:

| | Parts by weight |
|---|---|
| decylolcate | 25.0 |
| isopropyl myristate | 15.0 |
| and propylene glycol dicaprylate/ dicaprate | 5.0 |
| mineral oil | 54.85 |

B. An admixture is prepared by adding 0.01 pbw soluble melanin, e.g., as prepared as described in Example 3 or 4, to 0.01 pbw of "SOLERTAN PB-10" (a poly(propylene glycol) lanolin ether).

C. The admixture of part B is added to the admixture of part A and the resultant admixture is mixed until homogeneous.

D. The composition of part C is applied to the skin once or twice daily for two to four weeks.

EXAMPLE 8

Suntanning Lotion

An admixture was prepared containing the following:

| | Parts by weight |
|---|---|
| ICI G-1800 (e.g., poly[oxyethylene]21 stearyl ether) | 5.0 |
| isopropyl myristate | 10.0 |
| preservative | 0.1 |

-continued

|  | Parts by weight |
|---|---|
| stearyl alcohol | 2.0 |
| 2-hydroxy-3,3,5-trimethylhexyl ester of benzoic acid | 8.0 |
| butylated hydroxyanisole | 0.05 |

The above mixture is heated to 70° C. and 60 parts by weight of water, preheated to 70° C. is added thereto. The resultant mixture is stirred and allowed to cool to room temperature.

To the above mixture is then added a 1% citric acid solution, QS, to achieve a pH of 5.0 after which 0.01 parts by weight of a soluble melanin, for example, as prepared according to Example 3 or Example 4, is added, as well as sufficient deionized water to yield 100 parts by weight of lotion.

The above lotion is applied to the skin one-half (½) hour prior to exposure to the sun. After swimming, sweating or toweling, as well as after each hour of exposure, the lotion is reapplied.

The soluble melanin of the present invention can also be incorporated into foodstuffs as a coloring and/or flavoring agent, e.g. into coffee, tea, soda, beer, liquor, ice cream, frozen yogurt, barbecued potato chips, and the like. The amount added of course depends on the magnitude of the effect desired, but for liquids (beverages) it would be in the range of 1-1000 mg/liter and for solids (foodstuffs) it would be in the range of 1-1000 mg/kg. The amounts added would not be limited to these ranges.

It will be appreciated that the instant specification is set forth by way of illustration and not limitation, and that various modification and changes may be made without departing from the spirit and scope of the present invention.

We claim:

1. A melanin that is soluble in an aqueous solution at a pH of at least 5 to 9 at a temperature of 0° to 100° C., is capable of being filtered through at least a 0.45 micron size filter, is capable of being precipitated below pH 4, and has a molecular weight of greater than 10,000 daltons.

2. A melanin according to claim 1, wherein the pH is 6.5 to 7.5

3. A melanin according to claim 1, wherein the melanin remains soluble upon boiling.

4. A melanin according to claim 1, wherein the melanin remains soluble upon freezing/thawing.

5. A melanin according to claim 1, wherein the melanin exhibits a peak optical density at 310 to 320 nm and absorbs broadly throughout the visible and ultraviolet spectra.

6. An aqueous solution of the melanin according to claim 1.

* * * * *